(12) United States Patent
Yan

(10) Patent No.: US 7,113,286 B2
(45) Date of Patent: Sep. 26, 2006

(54) APPARATUS AND METHOD FOR IMPROVED ANALYSIS OF LIQUIDS BY CONTINUOUS WAVE-CAVITY RING DOWN SPECTROSCOPY

(75) Inventor: Wen-Bin Yan, Cranbury, NJ (US)

(73) Assignee: Tiger Optics, LLC, Warrington, PA (US)

( * ) Notice: Subject to any disclaimer, the term of this patent is extended or adjusted under 35 U.S.C. 154(b) by 341 days.

(21) Appl. No.: 10/727,939

(22) Filed: Dec. 3, 2003

(65) Prior Publication Data

US 2005/0122520 A1  Jun. 9, 2005

(51) Int. Cl.
*G01N 21/59* (2006.01)
(52) U.S. Cl. ........................ 356/436; 356/440
(58) Field of Classification Search ........ 356/436–438, 356/440
See application file for complete search history.

(56) References Cited

U.S. PATENT DOCUMENTS

| | | | |
|---|---|---|---|
| 3,770,354 A * | 11/1973 | Tsuruta et al. ............... | 356/435 |
| 5,528,040 A | 6/1996 | Lehmann | |
| 5,973,864 A | 10/1999 | Lehmann et al. | |
| 6,040,915 A * | 3/2000 | Wu et al. .................... | 356/435 |
| 6,368,560 B1 * | 4/2002 | Ostrander et al. .......... | 356/437 |
| 6,452,680 B1 * | 9/2002 | Paldus et al. ............... | 356/436 |
| 6,466,322 B1 | 10/2002 | Paldus et al. | |
| 2004/0207852 A1 * | 10/2004 | Bechtel et al. .............. | 356/440 |

OTHER PUBLICATIONS

Richard Engeln and Giel Berden, "Cavity Ring Down Absorption Spectroscopy", May 22, 2001, pp. 1-9.

Richard Engeln and Gerard Meijer, "A Fourier Transform Cavity Ring Down Spectrometer", Rev. Sci, Instrum. 67,2708 (1996), Dept. of Molecular and Laser Physics, University of Nijmegen, pp. 1-7.

A.J. Hallock, E.S.F. Berman, and R.N. Zare, "Use of Broadband, Continuous-Wave Diode Lasers in Cavity Ring-Down Spectroscopy for Liquid Samples", Jan. 10, 2003, Applied Spectroscopy, vol. 57, No. 5. 2003, pp. 571-573.

Alexander J. Hallock, Elena S.F. Berman, and Richard N. Zare, "Ultratrace Kinetic Measurements of the Reduction of Methylene Blue", Aug. 13, 2002, J. Am. Chem. Soc. vol. 125, No. 5. 2003, pp. 1158-1159.

K. J. Schulz and W. R. Simpson, "Frequency-Matched Cavity Ring-Down Spectroscopy", Chem. Phys. Lett. Oct. 14, 1998, Geophysical Institute and Chemistry Department, University of Alaska Fairbanks, pp. 1-9, Figure 1.

(Continued)

*Primary Examiner*—Richard A. Rosenberger
(74) *Attorney, Agent, or Firm*—RatnerPrestia

(57) ABSTRACT

An apparatus and method for analyzing an impurity in a liquid. The apparatus comprises a cell coupled to a light source and a detector. The cell includes a first mirror at a first end of the cell to receive and pass the light into the cell along a longitudinal axis of the cell, and a second mirror at a second end of the cell to at least partially reflect the light. A liquid supply device projects a stream of the liquid between the first mirror and the second mirror and across the longitudinal axis of the cell. The detector is coupled to the second end of the cell and determines a decay rate of the light within the cell based on the light passing through the liquid.

20 Claims, 4 Drawing Sheets

OTHER PUBLICATIONS

"Use of Broadband Light Source for CRDS", Office of Technology Licensing, Stamford University, Stamford Reference S02-221, 3 pages.

Synder et al., Cavity Ring-Down Spectroscopy as a Detector for Liquid Chromatography, Analytical Chemistry, vol. 75, No. 13, Jul. 1, 2003, pp. 3086-3091.

Xu et al., Cavity ring-down spectroscopy in the liquid phase, Review of Scientific Instruments, vol. 73, No. 2, Part 1, Feb. 2002, pp. 255-258.

International Search Report for PCT International Application No. PCT/US2004/040079, mailed Mar. 14, 2005.

* cited by examiner

APPARATUS AND METHOD FOR IMPROVED ANALYSIS OF LIQUIDS BY CONTINUOUS WAVE-CAVITY RING DOWN SPECTROSCOPY

FIELD OF THE INVENTION

This invention relates generally to absorption spectroscopy and, in particular, is directed to the detection of trace species in liquids using cavity ring-down cavity spectroscopy.

BACKGROUND OF THE INVENTION

Referring now to the drawing, wherein like reference numerals refer to like elements throughout, FIG. 1A illustrates the electromagnetic spectrum on a logarithmic scale. The science of spectroscopy studies spectra. In contrast with sciences concerned with other parts of the spectrum, optics particularly involves visible and near-visible light—a very narrow part of the available spectrum which extends in wavelength from about 1 mm to about 1 nm. Near visible light includes colors redder than red (infrared) and colors more violet than violet (ultraviolet). The range extends just far enough to either side of visibility that the light can still be handled by most lenses and mirrors made of the usual materials. The wavelength dependence of optical properties of materials must often be considered.

Absorption-type spectroscopy offers high sensitivity, response times on the order of microseconds, immunity from poisoning, and limited interference from molecular species other than the species under study. Various molecular species can be detected or identified by absorption spectroscopy. Thus, absorption spectroscopy provides a general method of detecting important trace species. In the gas phase, the sensitivity and selectivity of this method is optimized because the species have their absorption strength concentrated in a set of sharp spectral lines. The narrow lines in the spectrum can be used to discriminate against most interfering species.

In many industrial processes, the concentration of trace species in flowing gas streams and liquids must be measured and analyzed with a high degree of speed and accuracy. Such measurement and analysis is required because the concentration of contaminants is often critical to the quality of the end product. Gases such as $N_2$, $O_2$, $H_2$, Ar, and He are used to manufacture integrated circuits, for example, and the presence in those gases of impurities—even at parts per billion (ppb) levels—is damaging and reduces the yield of operational circuits. Therefore, the relatively high sensitivity with which water can be spectroscopically monitored is important to manufacturers of high-purity gases used in the semiconductor industry. Various impurities must be detected in other industrial applications. Further, the presence of impurities, either inherent or deliberately placed, in liquids have become of particular concern of late.

Spectroscopy has obtained parts per million (ppm) level detection for gaseous contaminants in high-purity gases. Detection sensitivities at the ppb level are attainable in some cases. Accordingly, several spectroscopic methods have been applied to such applications as quantitative contamination monitoring in gases, including: absorption measurements in traditional long pathlength cells, photoacoustic spectroscopy, frequency modulation spectroscopy, and intracavity laser absorption spectroscopy. These methods have several features, discussed in U.S. Pat. No. 5,528,040 issued to Lehmann, which make them difficult to use and impractical for industrial applications. They have been largely confined, therefore, to laboratory investigations.

In contrast, continuous wave-cavity ring-down spectroscopy (CW-CRDS) has become an important spectroscopic technique with applications to science, industrial process control, and atmospheric trace gas detection. CW-CRDS has been demonstrated as a technique for the measurement of optical absorption that excels in the low-absorbance regime where conventional methods have inadequate sensitivity. CW-CRDS utilizes the mean lifetime of photons in a high-finesse optical resonator as the absorption-sensitive observable.

Typically, the resonator is formed from a pair of narrow band, ultra-high reflectivity dielectric mirrors, configured appropriately to form a stable optical resonator. A laser pulse is injected into the resonator through a mirror to experience a mean lifetime which depends upon the photon round-trip transit time, the length of the resonator, the absorption cross section and number density of the species, and a factor accounting for intrinsic resonator losses (which arise largely from the frequency-dependent mirror reflectivities when diffraction losses are negligible). The determination of optical absorption is transformed, therefore, from the conventional power-ratio measurement to a measurement of decay time. The ultimate sensitivity of CW-CRDS is determined by the magnitude of the intrinsic resonator losses, which can be minimized with techniques such as superpolishing that permit the fabrication of ultra-low-loss optics.

FIG. 1B illustrates a conventional CW-CRDS apparatus 100 for measuring an impurity in liquid 111 contained within glass cell 109. As shown in FIG. 1B, light 104 is generated from a narrow band, tunable, continuous wave diode laser 102. Laser 102 is temperature and/or current tuned by a temperature and/or current controller (not shown) to put its wavelength on the desired spectral line of the impurity. Focusing lens (or lens system) 106 is positioned in line with light 104 emitted from laser 102. Light 104 exits focusing lens 106 and enters optical cell 112. Optical cell 112 includes mirror 108 at its input side and mirror 110 at its output side. As light 104 enters optical cell 112 it travels along the longitudinal axis of cell 112 and exponentially decays as it repeatedly travels between cell mirrors 108 and 110. The measure of this decay is indicative of the presence or lack thereof of an impurity in liquid 111 contained in glass cell 109.

Detector 114 is coupled between the output of optical cell 112 and processor 116. Processor 116 processes signals from optical detector 114 in order to determine the level of impurity in glass cell 109. A shortcoming of this system is that, although glass cell 109 is oriented at Brewster's angle with respect to light 104, refraction from the surface of glass cell 109 will deviate the path of light 104 away from Brewster's angle as it travels through liquid 111. Adjusting the orientation of glass cell 109 to compensate for the refraction will instead produce external reflection at the exterior surface of glass cell 109. Thus, the walls of glass cell 109, through which the light 104 must travel, inevitably introduce an additional interface which produces undesirable refractions. The result is increased signal loss which decreases sensitivity of the apparatus.

To overcome the shortcomings of conventional systems, an improved system and method for analyzing impurities in liquids using CW-CRDS is provided.

SUMMARY OF THE INVENTION

The present invention provides an apparatus and a method for quantitative measurement of an impurity in a liquid. The apparatus comprises a continuous wave-cavity ring-down spectrometer (CW-CRDS) equipped with a device to deliver a liquid stream into the cell between the first mirror and the second mirror of the CW-CRDS. The light escaping from the cell is monitored with a detector. The detector signal is output to a processor for analysis. When the wavelength of light transmitted into the cell is tuned to within the absorption spectra of the impurity, the processor relates the decay of the light within the cell to the concentration of the impurity in the liquid.

The angle at which the liquid stream is delivered with respect to the light is adjustable to reduce the external reflection (Fresnel reflection) of the light from the surface of the liquid stream. The ideal angle of intersection between the liquid stream and the light is known by those skilled in the art as Brewster's Angle.

For glass or other dielectric materials, there is a particular angle of incidence, called the polarizing angle (also called Brewster's angle, $\Theta_B$, because it was found experimentally by David Brewster), at which the reflection coefficient for the P-polarization component is zero. Thus, the light reflected from the glass, although of low intensity, is plane-polarized, with its plane of vibration at right angles to the plane of incidence. The P-polarization component at the polarizing angle is entirely refracted at angle of refraction $\Theta_r$; the S-polarization component is only partially refracted. Thus, the transmitted light, which is of high intensity, is only partially polarized.

Because the present invention delivers the liquid as a free stream across the light path there is no additional interference generated by one or more vessel walls. The presence of a vessel wall introduces an additional interface between the mirrors of the cell. Any refraction produced by this additional interface causes deviation of the light away from Brewster's angle on its path through the liquid and produces loss due to external reflection. When the vessel is thus eliminated, loss of light is reduced to that produced by the impurity and a small amount of scattering taking place at the liquid stream surface.

According to another aspect of the invention, a p-polarizer is introduced between the source and the detector.

According to a further aspect of the invention, the stream of liquid is projected freely into the cell.

According to yet another aspect of the invention, the CW-CRDS cell is substantially open to facilitate projection of the liquid stream across the light beam.

According to still another aspect of the invention, the apparatus is designed to permit adjustment to the angle of intersection between the liquid stream and the light beam to reduce external reflection of the light beam.

According to a yet further aspect of the invention, the processor is configured to determine the concentration of the impurity in the liquid based on the difference in ring-down rates between peak and off-peak wavelengths of the impurity.

According to another aspect of the invention, the processor is configured to determine the concentration of the impurity based on a whole peak profile.

According to a further aspect of the invention, the apparatus is also equipped with an optical splitter, a second cell, a second stream delivery device, and a second detector. A second liquid is introduced into the second cell for comparison with the liquid in the first cell. The second detector outputs its signal to the processor also receiving signal from the first detector. The processor then determines the concentration of the impurity in the first stream by comparing the data from each detector.

According to yet another aspect of the invention, the apparatus is also equipped with a second light source. The second light source can be tuned to a second wavelength for analysis of another impurity or for baseline comparison with the first wavelength.

According to still another aspect of the invention, the apparatus is also equipped with a second light source, a second stream delivery device, and a second detector. The first stream and the second stream are projected across both the first beam and the second beam to permit simultaneous measurement of the two streams in two wavelengths for analysis of multiple impurities or for comparison between the two streams.

It is to be understood that both the foregoing general description and the following detailed description are exemplary, but are not restrictive, of the invention.

BRIEF DESCRIPTION OF THE DRAWINGS

The invention is best understood from the following detailed description when read in connection-with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Figure 1A:
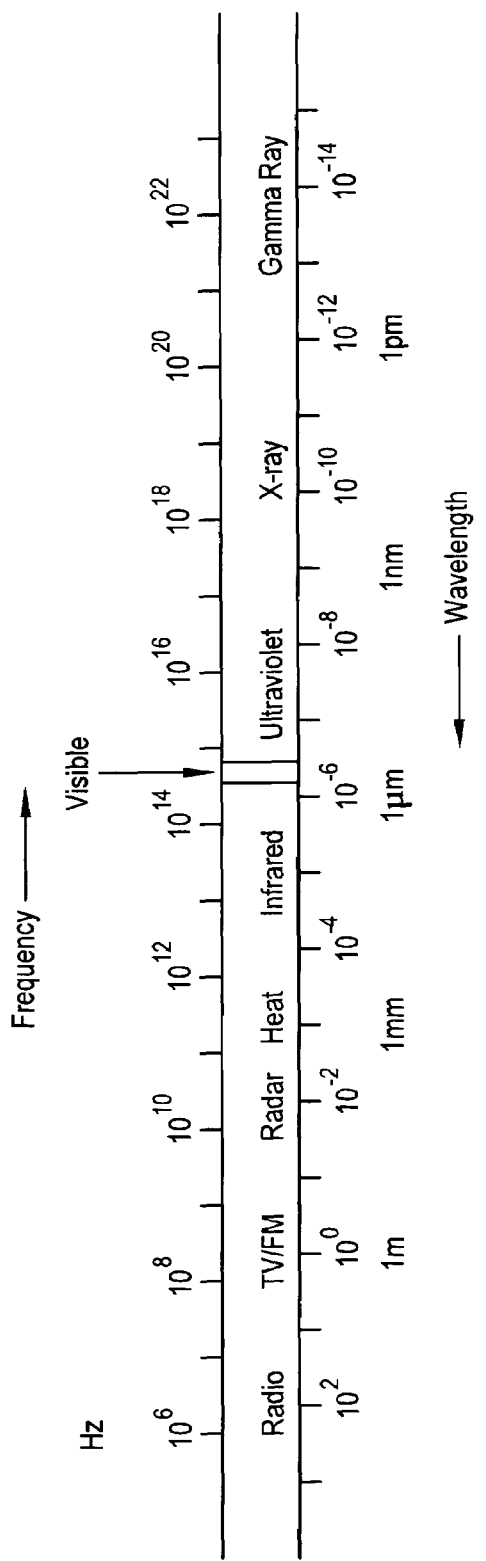
FIG. 1A illustrates the electromagnetic spectrum on a logarithmic scale.
Figure 1B:
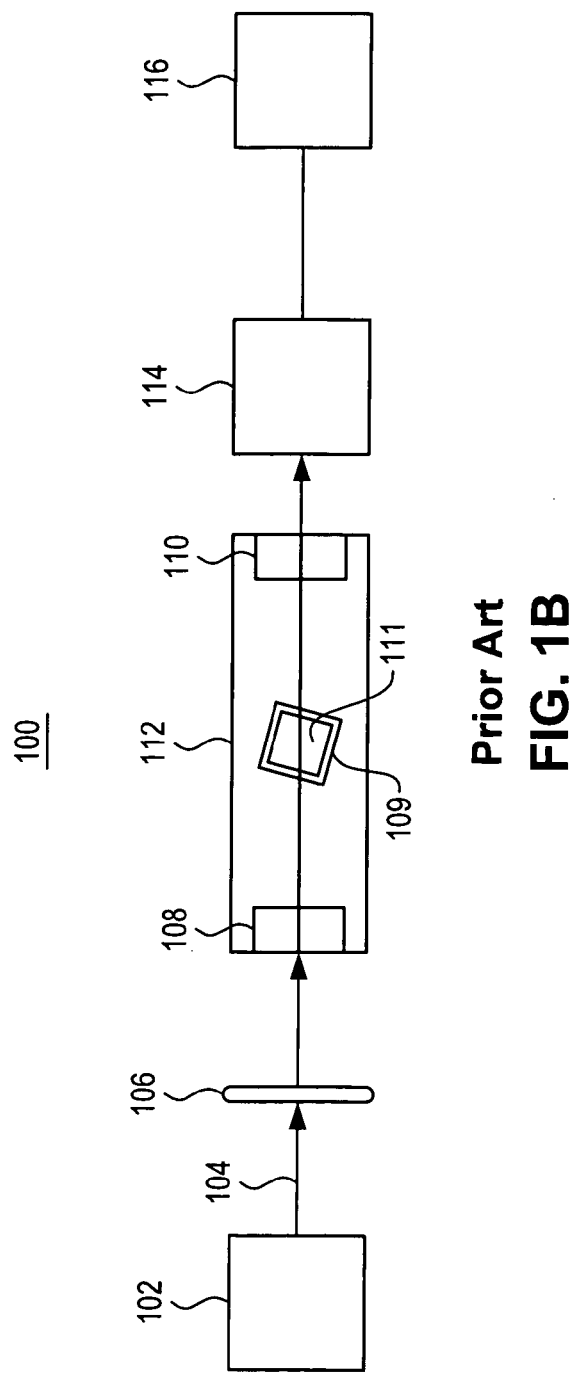
FIG. 1B illustrates a prior art CW-CRDS system for analysis of liquids.
Figure 2:
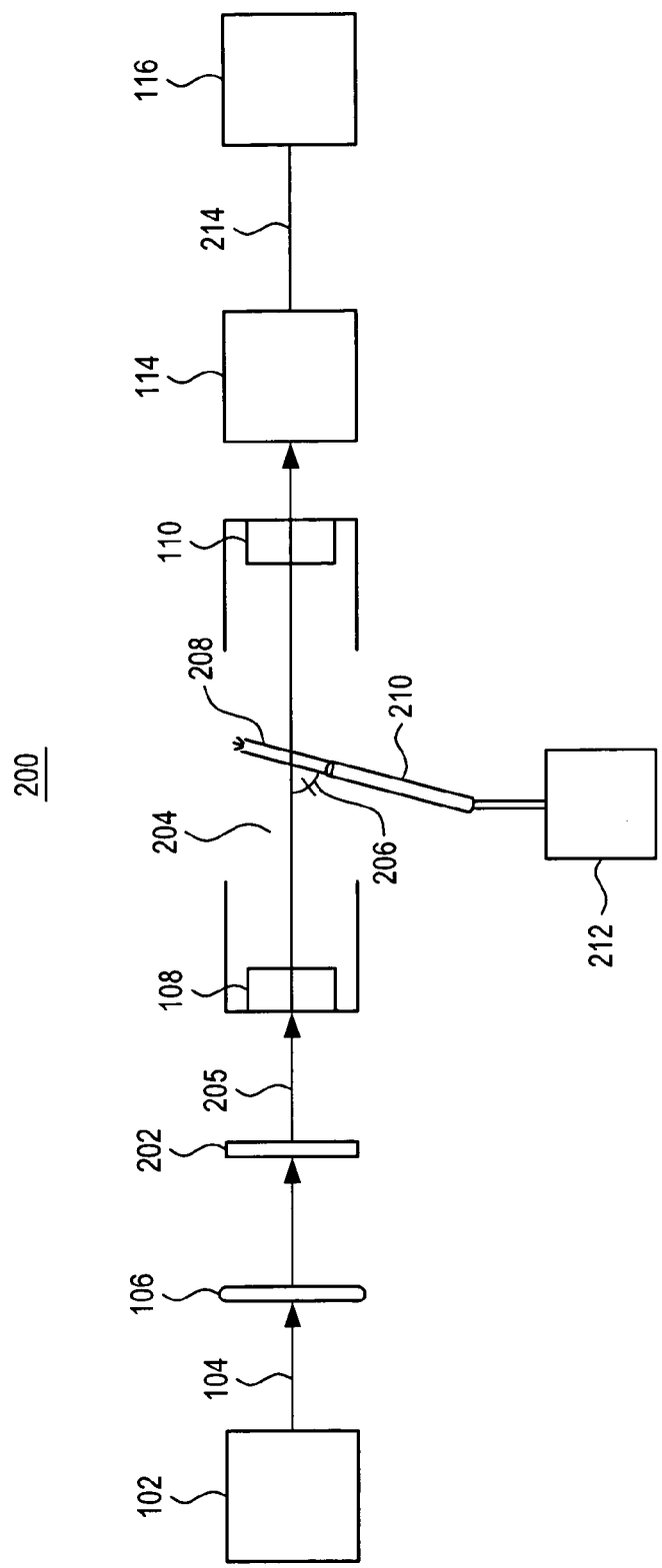
FIG. 2 illustrates an exemplary embodiment of the present invention.

FIG. 2 illustrates an exemplary embodiment 200 of the present invention. As shown in FIG. 2, light 104 is generated from the light source 102, such as a narrow band, tunable, continuous wave diode laser, for example. Light source 102 is temperature and/or current tuned by a temperature and/or current controller (not shown) to put its wavelength on the desired spectral line of the impurity of interest, such as a trace species. Light 104 is focused by focusing lens or lens system 106 and in-turn provided to p-polarizer 202 which polarizes light 104 in the p direction. P-polarized light 205 is transmitted from polarizer 202 to first cell mirror 108 and into cell 204, such as an open cell, along its longitudinal axis. Device 210, such as a liquid jet, for delivering a stream of liquid 208 is positioned to deliver liquid stream 208 between first mirror 108 and second mirror 110 and to intersect the longitudinal axis of cell 204 at an angle 206. In one embodiment angle 206 is adjusted to reduce external reflection of light 104. Preferably, angle 206 is set to or about complementary to Brewster's angle. In this case, since the jet is at Brewster's angle, the Fresnel reflection is minimized. Further, in one embodiment, liquid 208 is introduced into cell 204 in a free state, that is without being confined within a glass conduit or other restrictive element.

Device 210 is coupled to a pumping mechanism 212 or other source to deliver a substantially continuous flow of liquid 208 to device 210. Light 205 traveling through liquid stream 208 is reflected back along the longitudinal axis of cell 204 by second mirror 110. Detector 114, coupled to cell 204, monitors the decay rate of light 205 within cell 204 and provides an output signal 214 indicative of this decay rate. Processor 116 is coupled to detector 114 and configured to determine the level of one or more impurities or analytes in liquid stream 208. In a non-limiting example, this determination may be done by comparing a first ring-down rate measured at a wavelength selected a suitable distance from the peak profile of the impurity to a second ring-down rate measured at another wavelength selected within the peak profile of the impurity. An alternative example of the determination technique would be to perform a whole peak profile measurement, and fitting a lineshape. Although a p-polarizer 202 is illustrated in the exemplary embodiment, the invention is not so limited in that p-polarizer 202 is optional and may be eliminated if desired. Further, although the exemplary embodiment is described with respect to liquid impurities, the invention is also for the analysis of solid samples by dissolving them in a carrier liquid.

Figure 3:
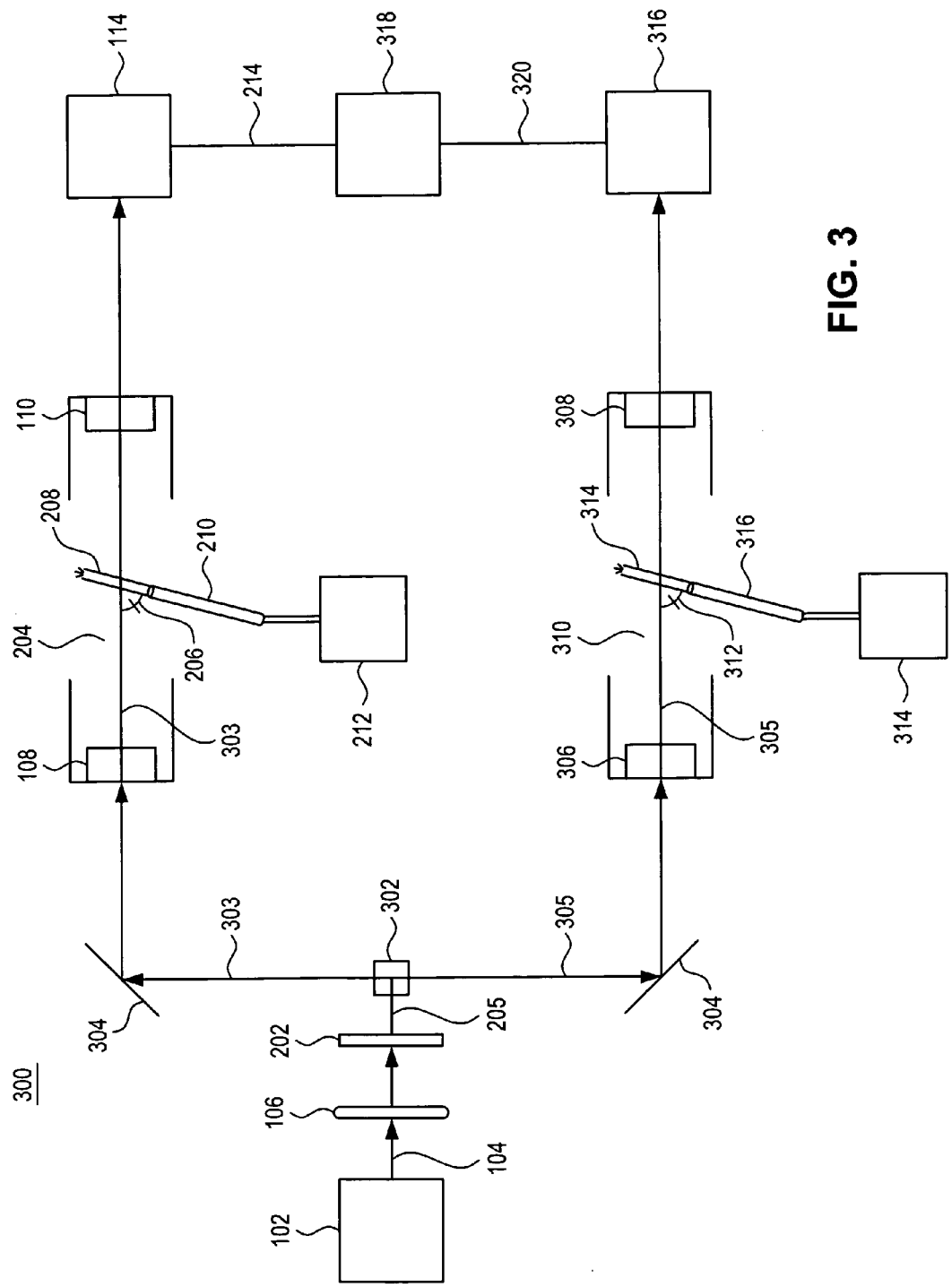
FIG. 3 illustrates another exemplary embodiment of the present invention.

FIG. 3 illustrates another exemplary embodiment 300 of the present invention. This embodiment further provides optical splitter 302, which splits light 104 into first beam 303 and second beam 305. The two beams are redirected, if necessary, by mirrors 304 toward respective cells 204 and 310. In one exemplary embodiment, first cell 204 and second cell 310 may be operated simultaneously. Second cell 310 is similar to cell 204 discussed above with respect to the first exemplary embodiment and includes first mirror 306 and second mirror 308. Second light beam 305 enters cell 310 through first mirror 306 and travels along a longitudinal path within cell 310. Device 316 delivers a second stream of liquid 314 between first mirror 306 and second mirror 308, and intersects light beam 305 at an angle 312. As is the first exemplary embodiment, angle 312 is adjusted to reduce external reflection of the light and is preferably adjusted to be complementary to Brewster's angle.

Device 316 is coupled to a pumping mechanism 314 or other source to deliver a substantially continuous flow of second liquid 314 to second device 316. The second liquid 314 may be a reference liquid substantially free of the impurity (or analyte) of interest, a second active sample of liquid for comparison with the first liquid, or another liquid sample for substantially simultaneous analysis, as desired. Second light beam 305 travelling through second liquid stream 314 is reflected back along the longitudinal axis of the cell 310 by second mirror 308. Second detector 316 coupled to second cell 310 and monitors the decay rate of second light beam 305 within second cell 310 and provides an output signal 320 indicative of this decay rate. Processor 116 is also coupled to both first detector 114 and second detector 316, and adapted to determine the level of impurity in one or both of streams 208, 314. In all other aspects, this exemplary embodiment is similar to the first exemplary embodiment.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. An apparatus for analyzing an impurity in a liquid for use with a light source, comprising:
    a cell coupled to the light source comprised of:
        a first mirror at a first end of the cell to receive a light from the light source and pass the light into the cell along a longitudinal axis of the cell, and
        a second mirror at a second end of the cell to at least partially reflect the light from the first mirror back along the longitudinal axis to the first mirror;
    a first liquid supply device adapted to freely project a first stream of the liquid between the first mirror and the second mirror and across the longitudinal axis of the cell; and
    a detector coupled to the second end of the cell and adapted to determine a decay rate of the light within the cell based on the light passing through the liquid.

2. The apparatus of claim 1, further comprising a polarizer coupled between the light source and the cell.

3. The apparatus of claim 1, wherein the cell is substantially open.

4. The apparatus of claim 1, wherein the liquid stream intersects the longitudinal axis of the cell at a predetermined angle so as to substantially reduce reflection of the light by the liquid stream.

5. The apparatus of claim 4, wherein the angle of intersection is complementary to Brewster's angle.

6. The apparatus of claim 1, further comprising a processor coupled to the detector to determine a level of the impurity in the liquid based on a decay rate of the light within the cell.

7. The apparatus of claim 6, wherein the processor is adapted to determine the level of the impurity in the liquid based on a difference between a first ring-down rate measured at an off-peak wavelength of a profile of the impurity and second ring-down rate measured at a peak wavelength of the profile of the impurity.

8. The apparatus of claim 6, wherein the processor is adapted to determine the level of the impurity in the liquid based on a whole peak profile measurement.

9. The apparatus of claim 1, further comprising:
    an optical splitter coupled to the light source to split the light from the light source into a first beam and a second beam, the cell coupled to the optical splitter
    a second cell coupled to the optical splitter, the second cell comprising:
        a first mirror at a first end of the second cell to receive the second beam and pass the second light beam into the second cell along a longitudinal axis of the second cell, and
        a second mirror at a second end of the second cell to at least partially reflect the light from second beam back along the longitudinal axis to the first mirror;
    a second liquid supply device adapted to project a second stream of a second liquid substantially free of the impurity into the second cell between the first mirror and the second mirror and across the longitudinal axis of the second cell; and
    a second detector coupled to the second end of the second cell and adapted to determine a decay rate of the second light within the second cell.

10. The apparatus of claim 9, further comprising a processor coupled to the first detector and the second detector, wherein the processor is adapted to determine the level of impurity in the liquid based on a difference between the decay rate in the cell and the second decay rate in the second cell.

11. A method for analyzing a trace species in a liquid for use with a light source, comprising the steps of:
    emitting a light from the light source;
    freely projecting a first stream of liquid across a path of the light emitted from the light source;
    passing the light through the first stream of the liquid;

measuring a decay rate of the light passing through the liquid; and determining a level of the trace species based on the decay rate.

12. The method of claim 11, further comprising the step of polarizing the light after the emitting step.

13. The method of claim 11 further comprises the steps of:
splitting the light from the light source into a first beam and a second beam;
passing the first beam through the first stream of liquid containing the trace species;
passing the second beam through a second stream of liquid substantially free of the trace species;
measuring a first decay rate of the first beam passing through the first stream of liquid;
measuring a second decay rate of the second beam passing through the second stream of liquid; and
determining the level of the trace species in the first steam of liquid based on a difference between the first decay rate and the second decay rate.

14. The method of claim 11, wherein determining an absorption spectrum of the trace species in the liquid is based on a difference between a first ring-down rate measured at an off-peak wavelength of a profile of the trace species and a second ring-down rate at a peak wavelength of the profile of the trace species.

15. The method of claim 11, wherein the determining step is based on a first whole peak profile measurement.

16. The method of claim 11, further comprising the step of projecting the first stream of liquid across the light at a predetermined angle.

17. The method of claim 16, wherein the predetermined angle is selected to reduce an external reflection of the light.

18. The method of claim 17, wherein the predetermined angle is about complementary to Brewster's angle.

19. An apparatus for analyzing a trace species in a liquid, comprising:
means for emitting a light;
means for freely projecting a first stream of liquid across a path of the light emitted from the light source:
means for passing the light through the first stream of liquid;
means for measuring a decay rate of the light passing through the first stream of liquid; and
means for determining a level of the trace species based on the decay rate.

20. An apparatus for analyzing a trace species in a liquid, comprising:
means for emitting a light;
means for splitting the light from the light emitting means into a first beam and a second beam;
means for freely projecting a first stream of liquid across a path of the first beam of light;
means for passing the first beam through the first stream of liquid containing the trace species;
means for passing the second beam through a second stream of liquid substantially free of the trace species;
means for measuring a first decay rate of the first beam passing through the first stream of liquid;
means for measuring a second decay rate of the second beam passing through the second stream of liquid; and
means for determining the level of the trace species in the first steam of liquid based on a difference between the first decay rate and the second decay rate.

* * * * *